US006966933B2

(12) United States Patent
Christensen (10) Patent No.: US 6,966,933 B2
(45) Date of Patent: Nov. 22, 2005

(54) PROSTHETIC FOOT WITH AN ADJUSTABLE ANKLE AND METHOD (75) Inventor: Roland J. Christensen, Fayette, UT (US)

(73) Assignee: Roland J. Christensen, as operating Manager of RJC Development, LC, General Partner of the Roland J. Christensen Family Limited Partnership, Fayette, UT (US)

( * ) Notice: Subject to any disclaimer, the term of this patent is extended or adjusted under 35 U.S.C. 154(b) by 0 days.

(21) Appl. No.: 10/690,941

(22) Filed: Oct. 21, 2003

(65) Prior Publication Data

US 2005/0085926 A1 Apr. 21, 2005

(51) Int. Cl.⁷ ................................. A61F 2/64
(52) U.S. Cl. ............................ 623/47; 623/38
(58) Field of Search .................... 623/47–56, 38

(56) References Cited

U.S. PATENT DOCUMENTS

| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,289,580 A | 12/1918 | Vincenti |
| 1,779,765 A | 10/1930 | Eichhorn |
| 1,996,874 A | 4/1935 | Mascau |
| 2,036,830 A | 4/1936 | Rowley |
| 2,379,538 A | 7/1945 | Meierhofer |
| 2,443,356 A | 6/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 6/1953 | Wisbrun |
| 2,843,853 A | 7/1958 | Mauch |
| 3,206,235 A * | 9/1965 | Albinson et al. ............. 403/90 |
| 3,551,914 A | 1/1971 | Woodall |
| 3,754,286 A | 8/1973 | Ryan |
| 3,871,032 A | 3/1975 | Karas |
| 3,874,004 A | 4/1975 | May |
| 3,906,552 A | 9/1975 | Weber |
| 3,920,610 A | 11/1975 | Wagner |
| 3,956,775 A | 5/1976 | Moore |
| 3,982,280 A | 9/1976 | Asbelle et al. |
| 4,089,072 A | 5/1978 | Glabiszewski |
| 4,328,594 A | 5/1982 | Campbell et al. |
| 4,442,554 A | 4/1984 | Copes |
| 4,506,395 A | 3/1985 | Haupt |
| 4,547,913 A | 10/1985 | Phillips |
| 4,636,220 A | 1/1987 | Ziegelmeyer |
| 4,645,509 A | 2/1987 | Poggi et al. |
| 4,676,800 A * | 6/1987 | Chen ........................... 623/38 |

(Continued)

FOREIGN PATENT DOCUMENTS

DE 295807 12/1916

(Continued)

*Primary Examiner*—Bruce E. Snow
(74) *Attorney, Agent, or Firm*—Thorpe North & Western (57) ABSTRACT

A prosthetic foot with an adjustable ankle includes an upper portion coupled to a socket of an amputee. A lower portion is adjustably coupled to the upper portion, and is attached to a foot member with heel and toe sections. A movable coupling is disposed between the upper and lower portions, and includes a displacement member slidably coupled to a displacement track. The movable coupling allows the toe section to pivot downward and the heel section to simultaneously displace forward.

10 Claims, 4 Drawing Sheets

U.S. PATENT DOCUMENTS

| | | | |
|---|---|---|---|
| 4,676,801 | A | 6/1987 | Lundeen |
| 4,721,510 | A | 1/1988 | Cooper et al. |
| 4,822,363 | A | 4/1989 | Phillips |
| 4,865,611 | A | 9/1989 | Al-Turaiki |
| 4,938,775 | A | 7/1990 | Morgan |
| 4,959,073 | A | 9/1990 | Merlette |
| 5,019,109 | A | 5/1991 | Voisin |
| 5,030,239 | A | 7/1991 | Copes |
| 5,037,444 | A | 8/1991 | Phillips |
| 5,112,356 | A | 5/1992 | Harris et al. |
| 5,116,383 | A | 5/1992 | Shorter et al. |
| 5,116,384 | A | 5/1992 | Wilson et al. |
| 5,156,632 | A | 10/1992 | Wellershaus |
| 5,181,932 | A | 1/1993 | Phillips |
| 5,181,933 | A | 1/1993 | Phillips |
| 5,217,500 | A | 6/1993 | Phillips |
| 5,219,365 | A | 6/1993 | Sabolich |
| 5,290,319 | A | 3/1994 | Phillips |
| 5,314,499 | A | 5/1994 | Collier, Jr. |
| 5,376,133 | A | 12/1994 | Gramnäs |
| 5,376,139 | A | 12/1994 | Pitkin |
| 5,376,141 | A | 12/1994 | Phillips |
| 5,387,246 | A | 2/1995 | Phillips |
| 5,425,781 | A | 6/1995 | Allard et al. |
| 5,425,782 | A | 6/1995 | Phillips |
| 5,443,528 | A | 8/1995 | Allen |
| 5,443,529 | A | 8/1995 | Phillips |
| 5,458,656 | A | 10/1995 | Phillips |
| 5,464,441 | A | 11/1995 | Phillips |
| 5,482,513 | A | 1/1996 | Wilson |
| 5,486,209 | A | 1/1996 | Phillips |
| 5,507,838 | A | 4/1996 | Chen |
| 5,509,936 | A | 4/1996 | Rappoport et al. |
| 5,509,938 | A | 4/1996 | Phillips |
| 5,514,185 | A | 5/1996 | Phillips |
| 5,514,186 | A | 5/1996 | Phillips |
| 5,549,714 | A | 8/1996 | Phillips |
| 5,571,210 | A | 11/1996 | Lindh |
| 5,571,213 | A | 11/1996 | Allen |
| 5,593,455 | A | 1/1997 | Phillips |
| 5,593,456 | A | 1/1997 | Merlette |
| 5,593,457 | A | 1/1997 | Phillips |
| 5,653,767 | A | 8/1997 | Allen et al. |
| 5,725,598 | A | 3/1998 | Phillips |
| 5,728,175 | A | 3/1998 | Rincoe |
| 5,728,176 | A | 3/1998 | Phillips |
| 5,728,177 | A | 3/1998 | Phillips |
| 5,746,774 | A * | 5/1998 | Kramer et al. ............ 623/39 |
| 5,766,265 | A | 6/1998 | Phillips |
| 5,769,896 | A | 6/1998 | Rosendahl et al. |
| 5,776,205 | A | 7/1998 | Phillips |
| 5,779,735 | A | 7/1998 | Molino |
| 5,800,564 | A | 9/1998 | Gelineau |
| 5,800,565 | A | 9/1998 | Biedermann |
| 5,800,569 | A | 9/1998 | Phillips |
| 5,824,112 | A | 10/1998 | Phillips |
| 5,888,238 | A | 3/1999 | Phillips et al. |
| 5,893,891 | A | 4/1999 | Zahedi |
| 5,899,944 | A | 5/1999 | Phillips |
| 5,913,902 | A | 6/1999 | Geible |
| 5,944,760 | A | 8/1999 | Christensen |
| 5,957,981 | A | 9/1999 | Gramnas |
| 5,976,191 | A | 11/1999 | Phillips |
| 5,993,488 | A | 11/1999 | Phillips |
| 6,019,795 | A | 2/2000 | Phillips |
| 6,071,313 | A | 6/2000 | Phillips |
| 6,120,547 | A | 9/2000 | Christensen |
| 6,165,227 | A | 12/2000 | Phillips |
| 6,187,052 | B1 | 2/2001 | Molino et al. |
| 6,197,068 | B1 | 3/2001 | Christensen |
| 6,206,934 | B1 | 3/2001 | Phillips |
| 6,228,124 | B1 * | 5/2001 | Slemker et al. ............ 623/47 |
| 6,241,776 | B1 | 6/2001 | Christensen |
| 6,254,643 | B1 | 7/2001 | Phillips |
| 6,261,324 | B1 | 7/2001 | Merlette |
| 6,280,479 | B1 | 8/2001 | Phillips |
| 6,290,730 | B1 | 9/2001 | Pitkin et al. |
| 6,306,178 | B1 | 10/2001 | Kania et al. |
| 6,402,790 | B1 | 6/2002 | Celebi |
| 2002/0133237 | A1 | 9/2002 | Christensen |

FOREIGN PATENT DOCUMENTS

| | | |
|---|---|---|
| GB | 1191633 | 5/1970 |
| GB | 1550658 | 11/1976 |
| IT | 556381 | 2/1957 |
| RU | 2033772 | 4/1995 |

\* cited by examiner

PROSTHETIC FOOT WITH AN ADJUSTABLE ANKLE AND METHOD

BACKGROUND OF THE INVENTION

1. Field of the Invention

The present invention relates generally to a prosthetic foot with an adjustable ankle. More particularly, the present invention relates to a prosthetic foot that simultaneously pivots downward and displaces forward.

2. Related Art

Many individuals have lost a limb for various reasons including war, accident, or disease. In most instances these individuals are not only able to live relatively normal lives, but physically active lives as well. Oftentimes, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element such as a spring. As the user steps onto the foot, the user's weight compresses the spring. As the user moves forward, the user's weight comes off the foot and the energy stored in the spring is used to propel the user forward.

Almost all of the past designs have focused on the major aspect of the prosthetic foot—movement of the ankle or foot as it relates to walking or running. Few designs consider the use of the foot with different shoes, such as different heel heights. For example, some shoes, such as sneakers, have a generally level or horizontally flat platform, while other shoes, such as high-heels or boots, have a heel that is relatively elevated with respect to the toe. It will be appreciated that the ankle of a natural foot pivots to accommodate different heels. In a natural foot, the foot and toes rotate to conform to the slope of the terrain. The artificial foot of previous designs usually incorporates a unitary foot that is incapable of such movement at the ankle.

Some artificial feet have a dynamic pivot or hinge at the ankle, or a dynamic ankle joint. See U.S. Pat. Nos. 4,442,554; 5,482,513 and 5,913,902. During use, a foot member often pivots or swings up and down about a pivot or axle.

Some artificial feet have an adjustable ankle with a swivel connection, or a foot that pivots at the ankle. For example, see U.S. Pat. Nos. 5,800,564 and 6,402,790. Such feet often have a foot member that selectively pivots about a pivot.

Other feet have a foot member that adjusts linearly back and forth. For example, see U.S. Pat. No. 6,228,124.

One problem with some of the above configurations is that they have proved unsatisfactory in use with different types of shoes, such as shoes with different heel heights. Another problem with some of the above configurations is that they are complicated or difficult to adjust.

SUMMARY OF THE INVENTION

It has been recognized that it would be advantageous to develop a prosthetic foot with an adjustable ankle. In addition it has been recognized that it would be advantageous to develop a prosthetic foot that provides a more natural feel or use when used with different shoes, such as shoes with different heel heights.

The invention provides an adjustable ankle device for a prosthetic foot. The adjustable ankle includes a lower portion adjustably coupled to an upper portion. The upper portion is coupled to a socket of an amputee. The lower portion is attached to a foot member with heel and toe sections. A movable coupling is disposed between the upper and lower portions. The lower portion moves: 1) simultaneously in a downward and forward direction in which the lower portion simultaneously pivots downward and displaces forward with respect to the upper portion; and 2) simultaneously in a rearward and upward direction in which the lower portion simultaneously pivots upward and displaces rearward with respect to the upper portion. In addition, the lower portion is pivotal and displaceable with respect to the upper portion between at least two fixed positions, including: 1) a low position configured to dispose the heel section at a lower elevational position, and to dispose the heel section in a rearward position; and 2) a high position configured to dispose the heel section at a higher elevational position, and to dispose the heel section in a forward position.

In accordance with a more detailed aspect of the present invention, the movable coupling can be oriented upright with respect to the lower portion, and can have at least one end disposed at a lower elevation with respect to a central section of the movable coupling. The movable coupling can also include a displacement member slidably coupled to a displacement track. The lower portion is movable from a rearward position to a forward and downward position, with the toe section pivoted downward and the heel section displaced forward.

In accordance with a more detailed aspect of the present invention, the movable coupling can include an arched coupling with an arcuate projection slidable in an arcuate slot. The arcuate projection is slidable in the arcuate slot in 1) a downward and forward direction in which the toe section pivots downward and the heel section simultaneously displaces forward with respect to the attachment member; and 2) a rearward and upward direction in which the toe section pivots upward and the heel section simultaneously displaces rearward with respect to the attachment member. In addition, the arcuate projection can be pivotal and displaceable with respect to the arcuate slot between at least two positions, including 1) a low position in which the toe section of the foot member is pivoted in an upward direction with respect to the arched coupling with the heel section disposed at a lower elevational position, and in which the heel section is disposed in a rearward position; and 2) a high position in which the toe section of the foot member is pivoted in a downward direction with respect to the arched coupling with the heel section disposed at a higher elevational position, and in which the heel section is disposed in a forward position.

Additional features and advantages of the invention will be apparent from the detailed description which follows, taken in conjunction with the accompanying drawings, which together illustrate, by way of example, features of the invention.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1–6, a prosthetic foot, indicated generally at 10, with an adjustable ankle, indicated generally at 14, in accordance with the present invention is shown for adjusting the prosthetic foot. The adjustable ankle 14 can adjust the angle of the foot 10, and the elevation of the heel. The adjustable ankle 14 can be utilized to quickly and easily adjust the foot 10 for use with different shoes, such as shoes with different heel heights. As described in greater detail below, the prosthetic foot 10 and adjustable ankle 14 allow the prosthetic foot to adjust by simultaneously pivoting downward and displacing forward. Thus, as a toe section pivots downward to accommodate a higher heel, the foot or heel also displaces forwardly. Surprisingly, it has been found that such a configuration provides a more natural feel.

The prosthetic foot 10 can have various different configurations. For example, the foot 10 can include one or more foot members 18 adjustably attached to an attachment member 22 by the adjustable ankle 14. Thus, the adjustable ankle 14 can be coupled between the attachment member 22 and the foot members 18. The attachment member 22 can be operatively coupled to a socket that receives an amputee's stump, as is known in the art. For example, the attachment member can include an inverted frustopyramidal boss 26 that can be received in a corresponding cavity (not shown), as is known in the art. Such inverted frustopyramidal type connections are typically used to selectively connect a prosthetic foot to the socket in a desired orientation, and can be used to adjust the angle between the foot and the socket. The boss 26 is held within a socket by a plurality of set screws, and is thus difficult to quickly adjust.

Figure 1:
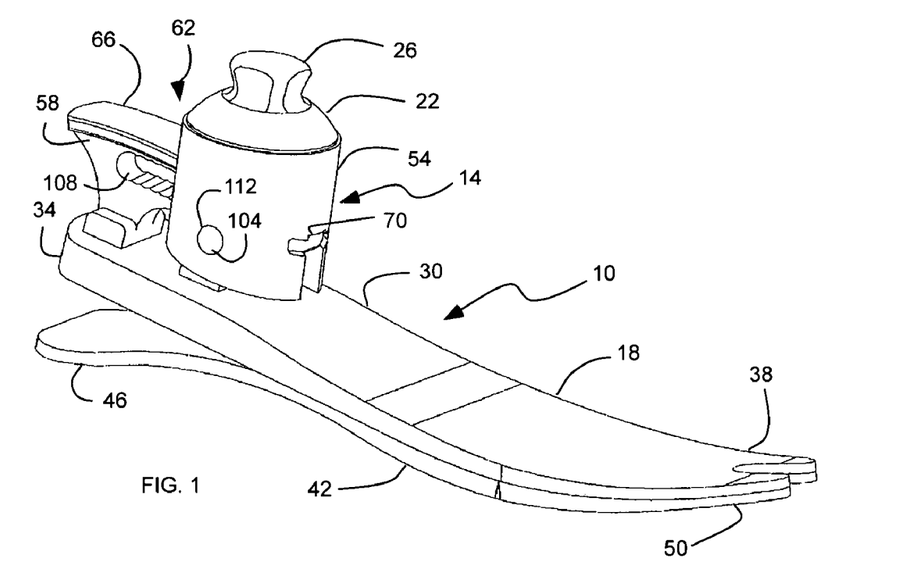
FIG. 1 is a perspective view of a prosthetic foot with an adjustable ankle in accordance with an embodiment of the present invention.
Figure 2A:
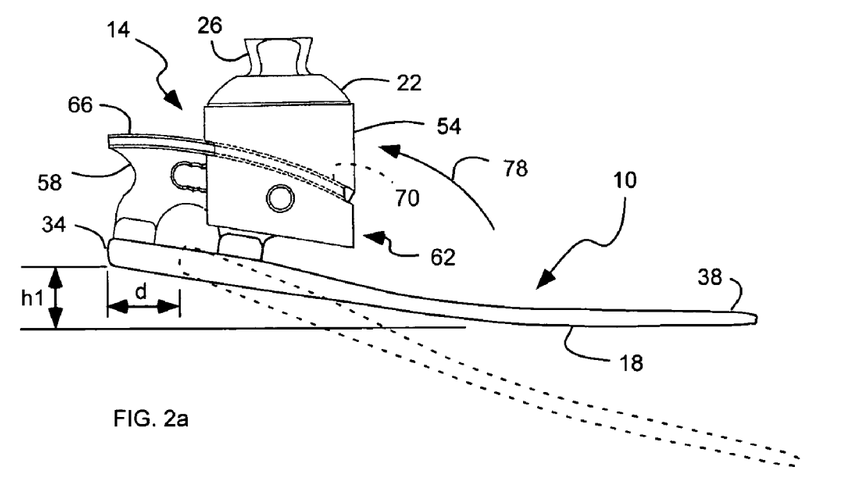
FIG. 2a is a side view of the prosthetic foot with an adjustable ankle of FIG. 1, shown in a first, lower position.
Figure 2B:
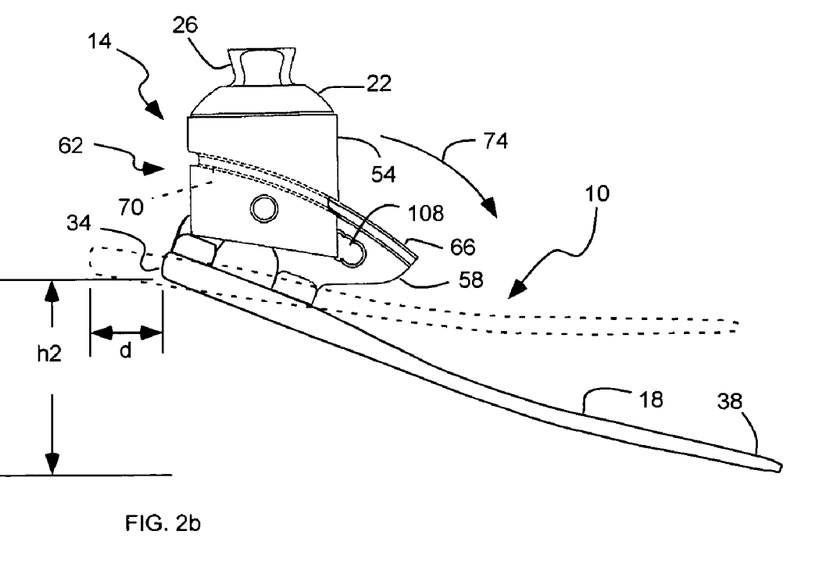
FIG. 2b is a side view of the prosthetic foot with an adjustable ankle of FIG. 1, shown in a second, higher position.

The foot members 18 can have various different members with various different configurations. For example, the foot members 18 can include a forefoot 30 that extends between a heel section 34 at a rear of the foot and a toe section 38 at a toe location of a natural foot. In addition, the foot members 18 can include a footplate 42 extending substantially the length of the foot between a heel section 46 at a heel location of a natural foot and a toe section 50 at the toe location. The toe section 50 of the footplate 42 can be attached to the toe section 38 of the forefoot 30. The foot members 30 and 42 can be flexible and resilient energy storing members that act as springs to bend or flex during use. The foot members 30 and 42 can include a composite material, such as a carbon or graphite fiber in an epoxy matrix.

Figures 3, 4, 7, 8:
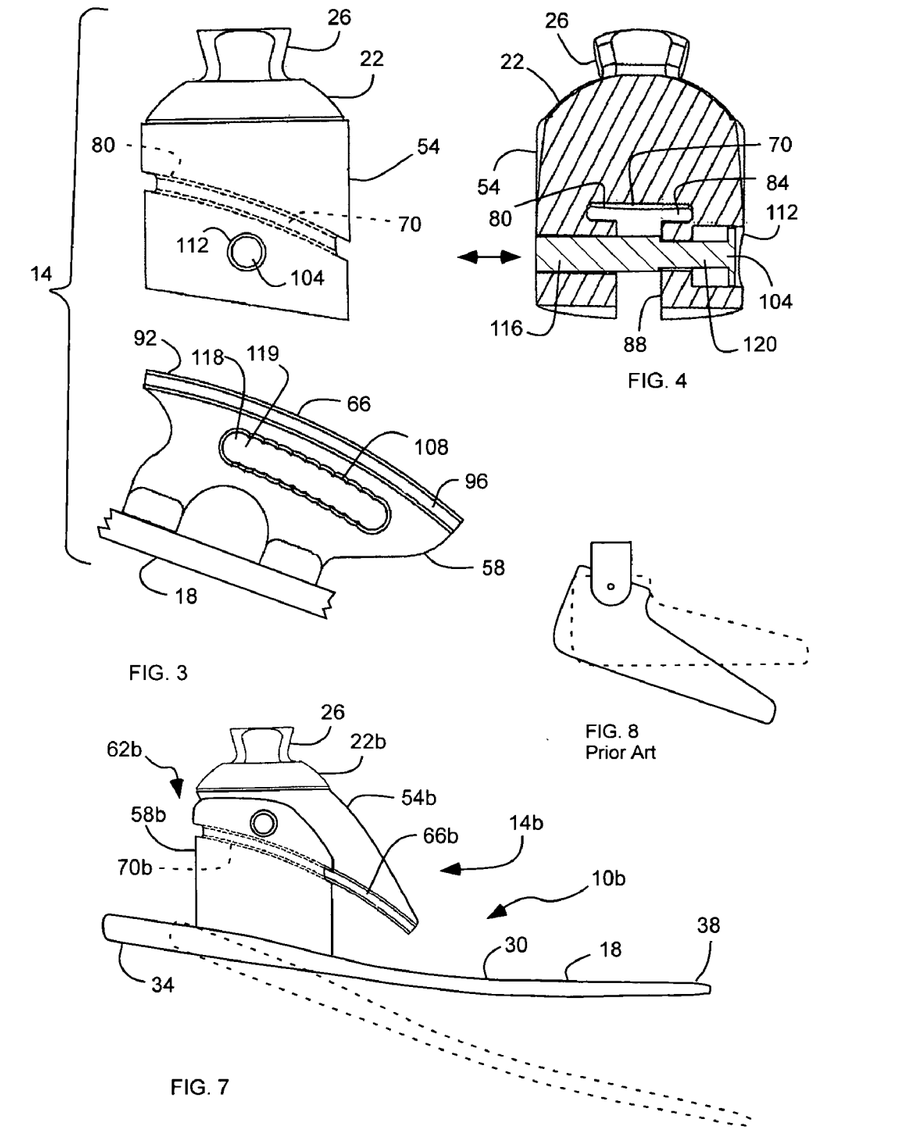
FIG. 3 is an exploded view of the adjustable ankle of FIG. 1.
FIG. 4 is a cross-sectional view of an upper portion of the adjustable ankle of FIG. 3.
FIG. 7 is a partial side view of another adjustable ankle in accordance with an embodiment of the present invention.
FIG. 8 is a side schematic view of a prosthetic foot with an adjustable ankle in accordance with the prior art.

The adjustable ankle 14 can include upper and lower portions 54 and 58 adjustably coupled to one another. The upper portion 54 can be coupled to the socket or attachment member 22. The upper portion 54 and attachment member 22 can be integrally formed, and the upper portion 54 can form part of the attachment member 22. The lower portion 58 can be coupled to the foot member 18 or forefoot 30.

A movable coupling is disposed between the upper and lower portions. The movable coupling allows the lower portion to move: 1) simultaneously in a downward and forward direction in which the lower portion simultaneously pivots downward and displaces forward with respect to the upper portion; and 2) simultaneously in a rearward and upward direction in which the lower portion simultaneously pivots upward and displaces rearward with respect to the upper portion. In addition, the lower portion is pivotal and displaceable with respect to the upper portion between at least two fixed positions, including: 1) a low position (FIG. 2a) configured to dispose the heel section at a lower elevational position, and to dispose the prosthetic foot or heel section in a rearward position; and 2) a high position (FIG. 2b) configured to dispose the heel section at a higher elevational position, and to dispose the prosthetic foot or heel section in a forward position.

The coupling can be oriented upright with respect to the lower portion 58, with one end of the coupling being disposed at a lower elevation with respect to a central section of the coupling. The movable coupling can include a displacement member slidable in a displacement track disposed between the upper and lower portions. The lower portion is movable from a rearward position to a forward and downward position, with the toe section pivoted downwardly and the heel section displaced forwardly. The movable coupling can include an arched coupling 62 formed or disposed between the upper and lower portions 54 and 58. The arched coupling 62 forms an arc that is oriented upright, with at least one end of the arched coupling or arc being disposed at a lower elevation with respect to a central section of the arched coupling. The arched coupling 62 includes an arcuate projection 66 slidable in an arcuate slot 70. The arcuate projection 66 can be or can form at least a portion of the lower portion 58, and thus can extend from the foot member 18 or forefoot 30. The arcuate slot 70 can be formed in the upper portion 54 or the attachment member 22. The arcuate projection 66 and arcuate slot 70 also have an upright orientation, as described above.

The arched coupling 62 (and the arcuate projection and slot 66 and 70) allows the arcuate projection 66 (and the lower portion 58 and foot portion 18) to both 1) pivot downward and 2) displace forward. Thus, the toe section 38 pivots downward and the heel section 34 simultaneously displaces forward (indicated by arrow 74 in FIG. 2b) with respect to the attachment member 22. Similarly, the arcuate projection 66 can both 1) pivot upward and 2) displace rearward. Thus, the toe section 38 pivots upward and the heel section 34 simultaneously displaces rearward (indicated by arrow 78 in FIG. 2a) with respect to the attachment member.

The foot member 18 is pivotal and displaceable between at least two positions, including 1) a low position and 2) a high position, as shown in FIGS. 2a and 2b. In the low position (FIG. 2a), the toe section 38 of the foot member 18 is pivoted in an upward direction 78 with respect to the arched coupling 62 (or attachment section 22). Thus, the heel section 34 (of attachment section 22) is disposed at a relatively lower elevational position h1 with respect to the high position (FIG. 2b). The low position can be used with flatter shoes, such as sneakers, flats, loafers and the like. In addition, the foot member 18 or heel section 34 is disposed in a rearward position, indicated by solid lines in FIG. 2a. In the low position, the forefoot 18 not only pivots upward, but displaces rearward so that the heel section 34, represented by d.

In the high position (FIG. 2b), the toe section 38 of the foot member 18 is pivoted in a downward direction 74 with respect to the arched coupling 62 (or attachment section 22). Thus, the heel section 34 (or attachment section 22) is disposed at a higher elevational position h2 with respect to the low position (FIG. 2a). Thus, the high position can be used with more elevated shoes, such as high heels, cowboy boots and the like. In addition, the foot member 18 or heel section 34 is disposed in a forward position, shown in solid lines, indicated by solid lines in FIG. 2b, as opposed to a rearward position. In the high position, the foot member 18 not only pivots downward, but displaces forward so that the heel section 34 is in a forward position, represented by d. Surprisingly, it has been found that as the elevation of the attachment section 22 is increased, a more forward position of the foot member 18 or heel section 34 provides a more natural feel. It will be appreciated that a simple pivot adjustment causes the foot to move rearward as it pivots downward, as shown in FIG. 8.

Figure 5:
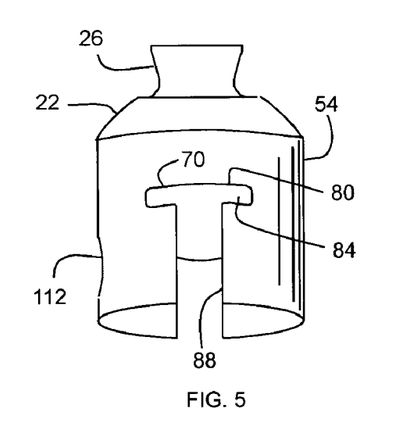
FIG. 5 is a front view of the upper portion of the adjustable ankle of FIG. 3.

As stated above, the arcuate slot 70 can be formed in the attachment section 22 or upper portion 54 of the arched coupling 62. The arcuate slot 70 can have an upper wall 80 that is arcuate or curved. In addition, the arcuate slot 70 can include an enlarged cavity 84 and a narrower gap 88. The enlarged cavity 84 is arcuate or curved. The narrower gap 88 can extend from a bottom of the upper portion 54 to the enlarged cavity 84. The arcuate slot 70 can have a T-shaped cross-section, with the enlarged cavity forming the upper horizontal portion of the T-shape, and the narrower gap 88 forming the lower vertical portion of the T-shape. In addition, the enlarged cavity 84 and narrower gap can extend entirely through the upper portion 54, or from the front to the back. As described above, the arc or curvature of the arcuate slot 70 and enlarged cavity 84 is oriented upright, or has at least one end that extends downward. In addition, the arc or curvature can be oriented to slope or angle downward towards the toe section 38.

Figure 6:
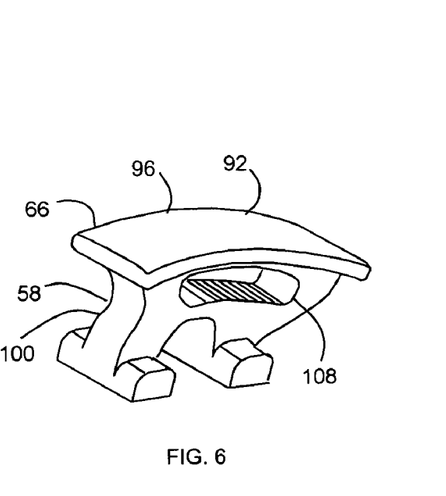
FIG. 6 is a perspective view of a lower portion of the adjustable ankle of FIG. 3.

The arcuate projection 66 can be formed on the lower portion 58 of the arched coupling 62, and can extend from the foot member 18. The arcuate projection 66 can have an upper wall 92 that is acruate or curved, with an arcuate or curved bearing surface that bears against the upper wall 80 of the arcuate slot 70 during use. The arcuate projection 66 can include an enlarged head or flange 96 and a narrower web 100. The enlarged head 96 is arcuate or curved. The narrower web 100 can extend from the bottom of the lower portion 58, or the foot member 18, to the enlarged head 96. The arcuate projection 66 can have a T-shaped cross-section with the enlarged head 96 forming the upper horizontal portion of the T-shape, and the narrower web 100 forming the lower vertical portion of the T-shape. The arcuate projection 66 and arucate slot 70 can be sized so that projection 66 can slide in the slot 70 with relatively little play. As described above, the arc or curvature of the arcuate projection 66 and enlarged head 96 is oriented upright. Thus, the arc or curvature of the arcuate projection 66 and enlarged head 96 (or bearing surface) can be convex, and can face upward and forward.

The adjustable ankle 14 with the arcuate projection 66 slidable in the arcuate slot 70 is one example of a means for movably coupling the lower portion 58 to the upper portion 54, or for movably coupling the foot member 18 with respect to the attachment member 22. In addition, the means for movably coupling can also be means for simultaneously 1) pivoting the lower portion 58, foot member 18 and/or toe section 38 downward with respect to the upper portion 54 or attachment member 22, and 2) displacing the lower portion 58, foot member 18 and/or heel section 34 forward with respect to the upper portion 54 or attachment member 22. Furthermore, the means for movably coupling can further be means for simultaneously 1) pivoting the toe section 38 of the foot member 18 downward with respect to the heel section 34, and 2) displacing the foot member 18 or heel section 34 forward with respect to the upper portion 54.

In addition, the adjustable ankle 14 with the arcuate projection 66 slidable in the arcuate slot 70 is one example of a means for selectively adjusting the elevational position of the heel section 34 with respect to the toe section 38 between at least two fixed positions, including 1) a low position (FIG. 2a) in which the heel section 34 is disposed at a lower elevational position with respect to the toe section 38, and in which the foot member 18 or heel section 34 is disposed in a rearward position with respect to the upper portion 54; and 2) a high position (FIG. 2b) in which the heel section 34 is disposed at a higher elevational position with respect to the toe section 38, and in which the foot member 18 or heel section 34 is disposed in a forward position with respect to the upper portion 54.

The adjustable ankle 14, and the arcuate projection 66 and arcuate slot 70, can have different configurations, including a dovetail-type connection. In addition, the heel section also can move up and down as the foot member pivots.

The adjustable ankle 14 also can include a locking mechanism that can be quickly operated to adjust the prosthetic foot 10. The locking mechanism can include a locking pin 104 and an elongated aperture 108. The aperture 108 can be formed in the lower portion 58, and the pin 104 can be disposed in a bore 112 on the upper portion 54. The aperture 108 can be formed by a plurality of overlapping bores so that a plurality of ridges are formed in the aperture to separate the aperture into discrete sections 118 interconnected by a channel 119. Thus, the pin can be disposed at a plurality of discrete positions. The pin 104 can include an enlarged portion 116 with a greater diameter for filling a discrete section and locking the arcuate projection 66 in the arcuate slot 70. The pin 104 can be displaced so that the enlarged portion 116 is displaced out of the discrete section and replaced by a smaller portion 120 with a smaller diameter that travels in the channel allowing the arcuate projection 66 to slide in the arcuate slot 70.

A method for adjusting a prosthetic foot, or using the prosthetic foot described above, includes pivoting a toe section 38 of a foot member 18 in a downward direction with respect to an attachment member 22 so that a heel section 34 of the foot member is disposed at a higher elevational position h2. In addition, the foot member 18 or heel section 34 is simultaneously displaced in a forward direction with respect to the attachment member 22 so that the heel section 34 is disposed at a greater forward position L2.

The above prosthetic foot 10, adjustable ankle 14, and arched coupling 62 have been described as having the arcuate slot 70 formed in the upper portion 54 or attachment section 22, and the arcuate projection 66 as part of the lower portion 58 or extending from the foot portion 18. This configuration can be reversed. Referring to FIG. 7, another prosthetic foot 10b is shown which is similar in many respects to that shown above, but with an arcuate projection 66b as part of the upper portion 54b, and an arcuate slot 70b formed in the lower portion 58b.

As described above, the attachment section 22 and upper portion 58 of the coupling 62 can be a single piece.

Figure 9:
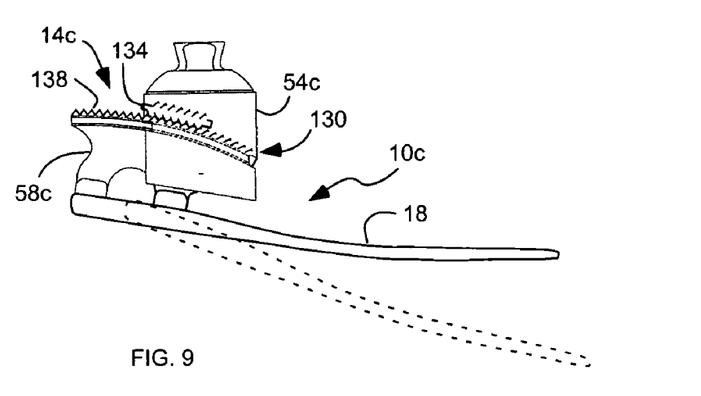
FIG. 9 is a side view of another adjustable ankle in accordance with an embodiment of the present invention.

Referring to FIG. 9, a prosthetic foot 10c is shown with an adjustable ankle 14c that is similar in some aspects to those described above. In addition, the adjustable ankle 14c can utilize a worm gear 130 to selectively adjust the elevational height of the ankle. The worm gear 130 can include a drive screw 134 on the upper portion 54c that engages screw threads 138 on the lower portion 58c. The drive screw 134 can be rotated, causing the lower portion 58c to both pivot and displace. The adjustable ankle 14c and/or worm gear 130 is another example of a means for movably coupling the lower portion 58c to the upper portion 54c, or for movably coupling the foot member 18c with respect to the attachment member. In addition, the means for movably coupling can also be means for simultaneously pivoting and displacing, as described above. In addition, the adjustable ankle 14c and worm gear 130 can form at least part of a means for selectively adjusting the elevational position of the heel section with respect to the toe section between at least two fixed positions, as discussed above.

Figure 10:
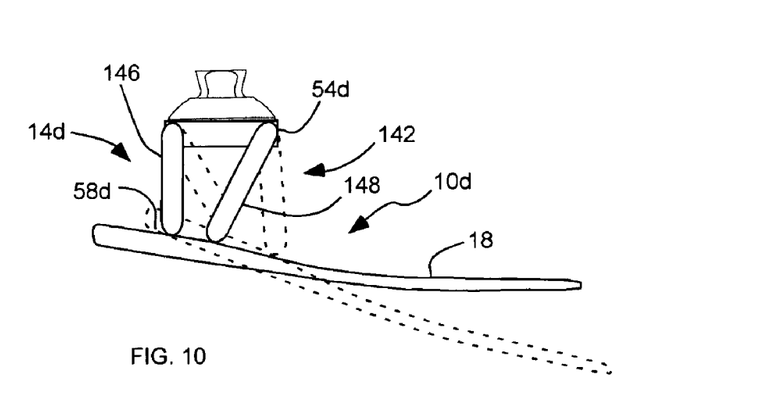
FIG. 10 is a side view of another adjustable ankle in accordance with an embodiment of the present invention.

Referring to FIG. 10, a prosthetic foot 10d is shown with an adjustable ankle 14d that is similar in some aspects to those described above. In addition, the adjustable ankle 14d can include a four bar linkage 142 to selectively adjust the elevational height of the ankle. The upper portion 54d or attachment member can form one of the links. Similarly, the lower portion 58d or foot member 18 can form another link. Another pair of links 146 and 148 can extend between the upper portion 54d and lower portion 58d or foot member 18. The links 146 and 148 can have different lengths, and/or have their ends attached at different lengths, in order to obtain the pivotal motion and displacement. The adjustable ankle 14d and/or four bar linkage 142 is another example of a means for movably coupling the lower portion 58d to the upper portion 54d, or for movably coupling the foot member 18d with respect to the attachment member. In addition, the means for movably coupling can also be means for simultaneously pivoting and displacing, as described above. In addition, the adjustable ankle 14d and four bar linkage 142 can form at least part of a means for selectively adjusting the elevational position of the heel section with respect to the toe section between at least two fixed positions, as discussed above.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A prosthetic foot device with an adjustable ankle, comprising:
   a) an attachment member configured to be coupled to a socket of an amputee; and
   b) a foot member, adjustably coupled with respect to the attachment member, having heel and toe sections; and
   c) an adjustable ankle, disposed between the foot member and the attachment member, including an arcuate projection with a convex bearing surface and a T-shaped cross-section slidable in an arcuate slot with a T-shaped cross-section.

2. A device in accordance with claim 1, wherein the foot member is pivotal and displaceable with respect to the attachment member between at least two fixed positions, including:
   a) a low position in which the heel section is disposed at a lower elevational position and in which the heel section is disposed in a rearward position relative to the attachment member; and
   b) a high position in which the heel section is disposed at a higher elevational position and in which the heel section is disposed in forward direction relative to the attachment member.

3. A device in accordance with claim 1, wherein the arcuate slot is formed in the attachment member; and wherein the arcuate projection extends from the foot member.

4. A device in accordance with claim 1, further comprising:
   a) an aperture, formed in the projection; and
   b) a locking pin, disposable in the aperture.

5. An adjustable ankle device for a prosthetic foot, comprising:
   a) an upper portion configured to be coupled to a socket of an amputee; and
   b) a lower portion, adjustably coupled to the upper portion, configured to be attached to a foot member with heel and toe sections; and
   c) an adjustable ankle, disposed between the upper and lower portions, having a constrained and arcuate movement path limiting both pivotal movement and displacement of the lower portion with respect to the upper portion to the arcuate movement path, and oriented so that the lower portion is limited to simultaneously pivot and displace forward and downward, or rearward and upward; and
   d) the adjustable ankle including an arcuate projection with a T-shaped cross-sectional shape slidable in arcuate slot with a T-shaped cross-sectional shape.

6. A device in accordance with claim 5, wherein the arcuate projection includes a convex bearing surface.

7. A device in accordance with claim 5, further comprising:
   a) an aperture, formed in the arcuate projection; and
   b) a locking pin, disposable in the aperture.

8. An adjustable ankle device for a prosthetic foot, comprising:
   a) an upper portion configured to be coupled to a socket of an amputee; and
   b) a lower portion, adjustably coupled to the upper portion, configured to be attached to a foot member with heel and toe sections; and c) a movable coupling, disposed between the upper and lower portions, having an arcuate movement track and constraining both pivotal and displacement movement of the lower portion with respect to the upper portion to the arcuate displacement track so that the lower portion is limited to move:
  i) simultaneously in a downward and forward direction in which the lower portion simultaneously pivots downward and displaces forward with respect to the upper portion; and
  ii) simultaneously in a rearward and upward direction in which the lower portion simultaneously pivots upward and displaces rearward with respect to the upper portion; and
d) the lower portion being pivotal and displaceable with respect to the upper portion between at least two fixed positions, including:
  i) a low position configured to dispose the heel section at a lower elevational position and to dispose the heel section in a rearward position relative to the upper portion; and
  ii) a high position configured to dispose the heel section at a higher elevational position and to dispose the heel section in a forward position relative to the upper portion;
e) the movable coupling further including an arched coupling oriented upright with respect to the lower portion and having at least one end of the arched coupling being disposed at a lower elevation with respect to a central section of the arched coupling, and including an arcuate projection with a T-shaped cross-sectional shape slidable in an arcuate slot with a T-shaped cross-sectional shape.

9. A device in accordance with claim 8, wherein the arcuate projection includes a convex bearing surface.

10. A device in accordance with claim 8, further comprising:
  a) an aperture, formed in the arcuate projection; and
  b) a locking pin, disposable in the aperture.

* * * * *